United States Patent [19]

Nouri

[11] Patent Number: 5,013,311
[45] Date of Patent: May 7, 1991

[54] ENVELOPE GENERATOR FOR A POWER BEAM

[75] Inventor: Taoufik Nouri, Oberhofen, Switzerland

[73] Assignee: Lasag AG, Thun, Switzerland

[21] Appl. No.: 417,599

[22] Filed: Oct. 5, 1989

[30] Foreign Application Priority Data

Oct. 6, 1988 [CH] Switzerland .................. 3746/88

[51] Int. Cl.⁵ .............................................. A61N 5/02
[52] U.S. Cl. ........................................ 606/4; 606/13;
606/16; 606/17; 128/395; 128/897
[58] Field of Search .............. 128/395, 397, 398, 897;
606/2, 4–19

[56] References Cited

U.S. PATENT DOCUMENTS

| | | | |
|---|---|---|---|
| 3,710,798 | 1/1973 | Bredemeier | 128/303.1 |
| 4,391,275 | 7/1983 | Fankhauser et al. | 128/303.1 |
| 4,409,979 | 10/1983 | Roussel et al. | 128/303.1 |
| 4,565,197 | 1/1986 | Daly | 128/303.1 |
| 4,724,317 | 2/1989 | Brown et al. | 250/231.1 |

FOREIGN PATENT DOCUMENTS

215698 11/1984 Fed. Rep. of Germany ........ 606/11

Primary Examiner—Stephen C. Pellegrino
Assistant Examiner—David Shay
Attorney, Agent, or Firm—Griffin, Branigan & Butler

[57] ABSTRACT

The arrangement of this invention concerns a surgical apparatus, in particular for ophthalmological use. In addition to a power beam it includes a beam of coherent visible light (29) which is transformed into at least one elementary beam (30) by means of a homogeneous light guide (21). The guide, which may be an optical fiber, is fixed to a rotating element (33) rotating about an axis (2). When the element rotates the elementary beam generates a luminous tubular beam intended to surround the power beam, the whole then being focussed by a lens to a point terminating a treatment cone with a predetermined vertex angle. The rotating element may include means for varying the diameter of the luminous tubular beam such as a transporter (39) bearing one end of the optical fiber and responding to the operation of a screw (45). The arrangement permits, on one hand to localize a point of treatment in the eye and, if necessary, modification of the vertex angle of the treatment cone.

16 Claims, 6 Drawing Sheets

ENVELOPE GENERATOR FOR A POWER BEAM

This invention concerns a surgical treatment device, in particular for ophthalmological purpose comprising:

at least one first light source emitting a power beam along a first optical axis and having a predetermined cross-section, a second light source emitting a visible light beam along a second optical axis, a rotating element rotating around said second optical axis, said element including means for transforming the beam issuing from said second source into at least one elementary beam turning around said second optical axis and arranged to form a luminous tubular beam intended to surround said power beam, means for combining said power beam and said luminous tubular beam along a third common optical axis, and a lens arranged in the path of the third optical axis so as to concentrate said power beam and said luminous tubular beam which surrounds it onto the focal point of the lens in accordance with a cone having a predetermined vertex angle.

The invention also concerns an arrangement such as defined above in which the first light source emits a variable cross-section power beam.

BACKGROUND OF THE INVENTION

Such arrangements have been described in patent document EP-B-O 030 210. Such arrangements incorporated into an apparatus for the observation of an eye in view of subsequent treatment by laser surgery permit not only to visualize the power beam which is itself invisible but also to check that no obstacle (such as the iris, for instance), is found in the path of said beam.

This prior art will now be briefly reviewed. For this purpose FIG. 1 herein will be referred to.

Figure 1:
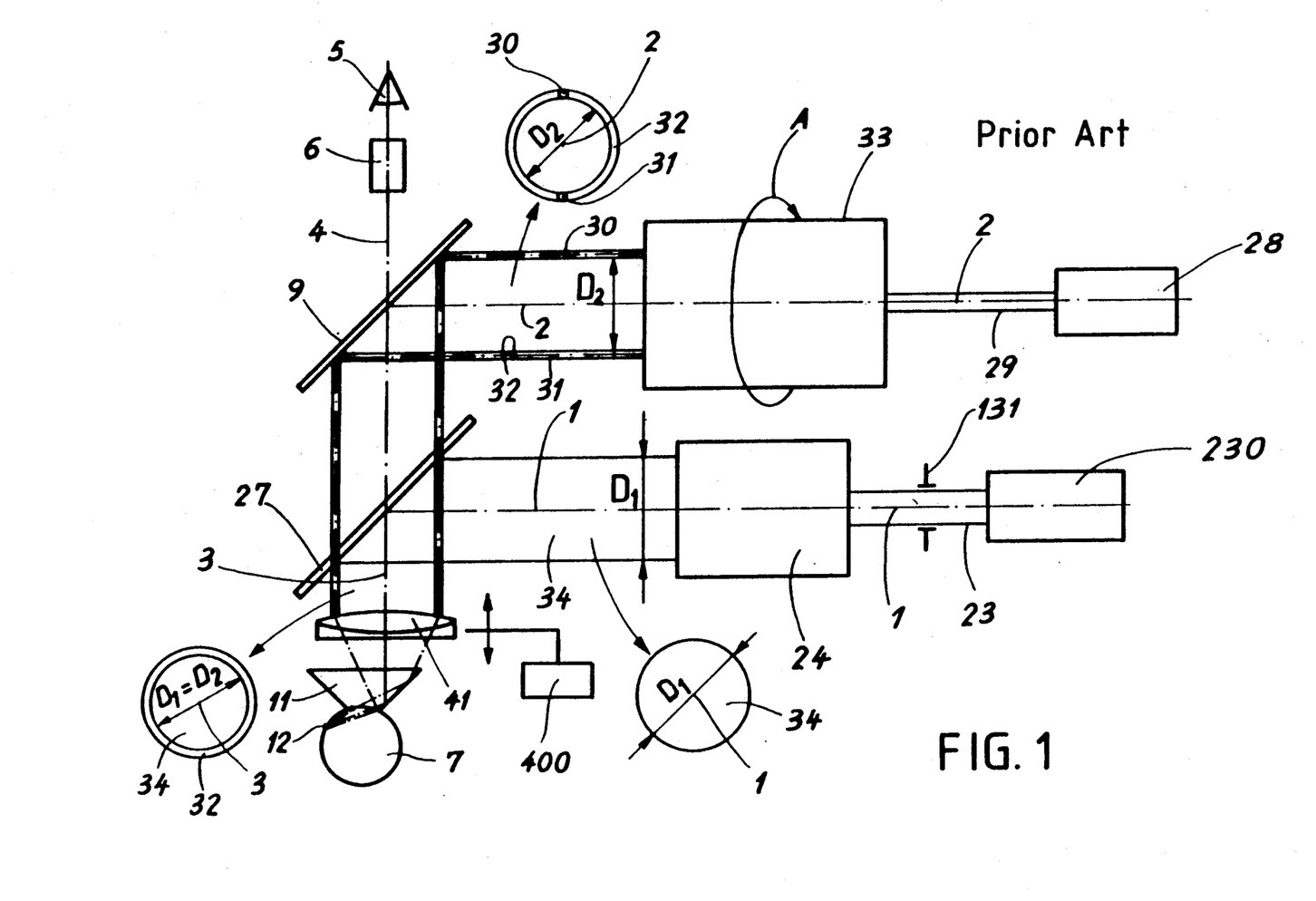
FIG. 1 is a schematic sketch showing the prior art as explained hereinabove.

The apparatus includes a first light source 230 which emits a power beam 23 intended for surgical treatment. This beam is emitted along a first optical axis 1 from for instance a solid state laser source operating in a pulsed mode (for example in the so-called Q switching mode). The cross-section of the beam may be modified either by means of a diaphragm with an iris 131 or by optical adaptation means here symbolized by block 24. At the output of these elements the beam propagating along axis 1 exhibits a predetermined cross-section. This section here is cylindrical having a diameter $D_1$. However, in a known manner, it could also be for instance square or rectangular.

The apparatus further includes a second light source 28 which emits a visible light beam 29 of low power. This beam is emitted along a second optical axis from for instance a He-Ne laser. The beam 29 is received by an arrangement including a rotatable element 33 turning for instance in the sense of arrow A, around the second optical axis 2. This element includes in the cited document, a set of prisms and mirrors transforming the beam 29 into two elementary parallel beams 30 and 31. When the element 33 rotates the elementary beams generate a luminous tubular beam 32 having a diameter $D_2$ and co-axial with the second optical axis 2. The rotatable element is arranged in a manner such that the diameter $D_2$ of the tubular beam 32 is equal to the diameter $D_1$ of the power beam 34. This adaptation is brought about in the cited document by a sliding lever controlling two prisms. From each of these prisms is emitted an elementary beam, said beams being adapted to be spread apart or brought together through manipulation of the lever.

FIG. 1 further shows that the apparatus is provided with two half-reflecting mirrors 9 and 27 which have as purpose to combine the power beam 34 and the luminous tubular beam 32 along a third optical axis 3 in a manner such that beam 32 surrounds beam 34.

In the path of the third optical axis 3 is arranged a lens 41 which may be axially displaced by means of a mechanism 400 which serves to adjust the focal point of the lens onto the place to be treated or to be observed.

Thus, at the output of lens 41 is found a light cone the vertex angle of which is predetermined on the one hand by the focal length of the lens and on the other hand by diameters $D_1$ and $D_2$ of beam 34 and beam 32 respectively. The cone of the beam 34 is then surrounded by an envelope cone issuing from beam 32.

The focal point of lens 41 may be observed by a practitioner 5. The eye of the practitioner bears on an optical complex 6 which defines an observation beam 4 finally being superposed onto the optical axis 3. This complex may also be a binocular type system.

The luminous output cone of lens 41 is deviated by a contact lens 11 which the practitioner supports on the eye 7 of the patient in a manner such that the focal point 12 of said lens falls at the desired location.

The reader may refer to the cited document in order to obtain still further details concerning the operation of the entire system. One may recall here simply that the observation beam is provided with a large depth of field and that consequently the visual observation is insufficient to locate with precision the position of the focal point of lens 41 which explains the presence of the second light source 28 so as to enable an extremely precise positioning of the focal point of the power beam 34. It will be noted in passing that this second source may be coherent or non-coherent.

As has been mentioned hereinabove, the rotating element 33 includes a set of prisms and mirrors. In practice, the manufacture, assembly and regulation of such elements is extremely expensive. Furthermore, such equipment is heavy and voluminous which increases the weight and space occupied by the arrangement.

SUMMARY OF THE INVENTION

To overcome these difficulties, this invention proposes to eliminate the set of prisms and mirrors forming part of the rotating element in a manner such that it is characterized in a first embodiment by the fact that the means for transforming the beam issuing from the second luminous source into at least one elementary beam turning about the second optical axis includes at least one homogeneous light guide.

As has already been mentioned hereinabove, the arrangement according to the prior art includes a possible adaptation of the diameter of the tubular beam to the diameter of the power beam. This adaptation is brought about from outside the element in rotation by means of prisms and by a lever controlling such prisms. This system likewise presents the difficulty of being difficult to manufacture, to assemble and to regulate.

Thus, to overcome these difficulties, this invention proposes to include in the rotating element an arrangement enabling the adaptation of the diameters. To this end, it includes, in addition to the feature included in the first embodiment, second means forming part of the rotating element in order to bring about variation of the diameter exhibited by the tubular luminous beam in a manner such that it surrounds the power beam in correspondence with the chosen cross-section for said power beam.

In summary and in view of the characteristics mentioned hereinabove, the arrangement according to the invention enables the employment of means which are lighter, more flexible, less fragile and less costly than those employed in the prior art without in any way sacrificing either precision or reliability.

The invention will be better understood with the aid of the description to follow, given solely by way of example, and by referring to the drawings.

DESCRIPTION OF THE PREFERRED EMBODIMENTS

Figure 2:
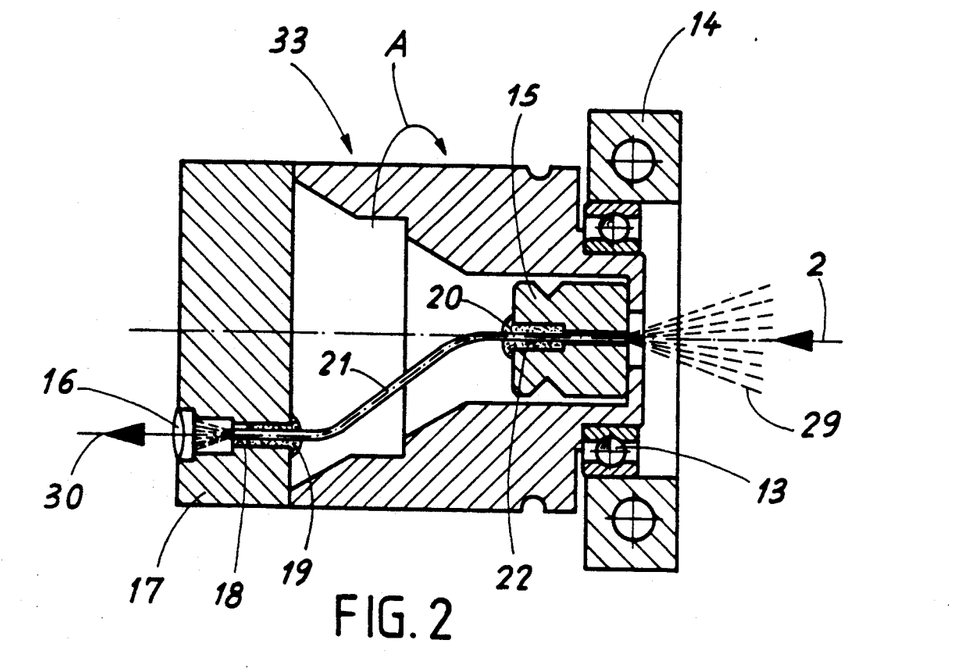
FIG. 2 is a cross-section through the rotating element referenced 33 on FIG. 1 and obtained in accordance with a first embodiment of the invention.

The rotating element 33 shown on FIG. 2 is a drum turning in the sense of arrow A. This element 33 is inserted in the schematic of FIG. 1 in the place of the block bearing the same reference. Means are employed in order to drive the drum in rotation and such means will be explained subsequently, for instance through reference to FIGS. 4 and 5. The drum turns in a fixed frame 14 to which it is attached via a ball bearing 13. The axis of rotation of the drum is merged with the second optical axis 2, said second axis being that of the light beam 29 emitted by the second light source 28 as has been explained with reference to FIG. 1. According to the invention, beam 29 penetrates into a homogeneous light guide 21. As shown on FIG. 2, the beam 29 is transformed into an elementary beam 30 offset relative to the second axis 2 and parallel to this axis. When the drum turns, the elementary beam 30 generates a tubular luminous beam 32 (see FIG. 1). An end of the guide 21 penetrates into an orifice 22 pierced in a cylindrical element 15 integral with the drum, such end receiving beam 29. The other end of the guide 21 penetrates into a second orifice 18 pierced into the front wall 17 of the drum. In the orifice 18 is placed a lens 16 intended to render parallel the light emerging from the guide 21 and forming the elementary beam 30. The guide 21 is maintained in the orifices 18 and 22 by means of glue points referenced respectively 19 and 20. In the particular case shown on FIG. 2, the homogeneous light guide 21 is nothing more than a simple optical fiber well known in itself as for instance in the telecommunication domain. In this precise case it is seen that the tubular luminous beam 32 (FIG. 1) is generated by a single elementary beam 30 produced by a single guide 21, such elementary beam turning around axis 2.

Figure 3:
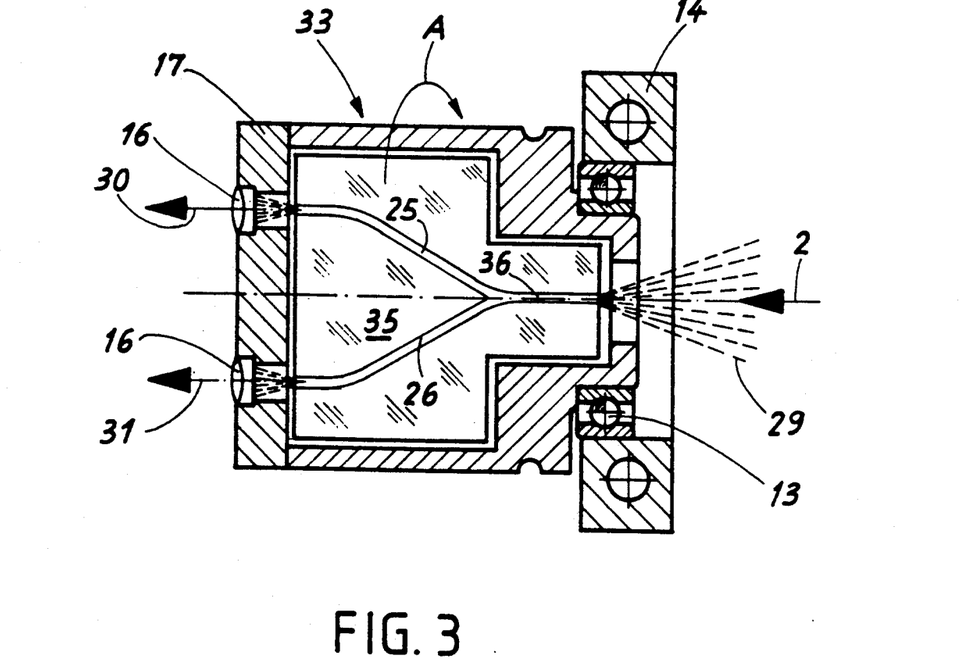
FIG. 3 is a cross-section through the rotating element referenced 33 in FIG. 1, and obtained in accordance with a variant of the first embodiment of the invention.

FIG. 3 is a cross-section through the rotating element 33 obtained in accordance with a variant of the first embodiment of the invention as described hereinabove. In this case, the drum bears means for transforming the beam 29 into two elementary beams 30 and 31, such means consisting of employing two homogeneous light guides 25 and 26. In this particular embodiment, there is arranged at the interior of the drum a glass plate 35 in which there are formed channels 25, 26 and 36 by doping said plate, such doping being obtained by means of germanium or potassium salts for instance. The channel 36 here is divided into two branches 25 and 26. The input of channel 36 receives beam 29 and at each of the outputs of channels 25 and 26 there is arranged a lens 16 enabling, as has already been mentioned, to render parallel the light beams emerging from these channels. In turning, the drum generates thus a tubular luminous beam 32 (FIG. 1) issuing this time in the form of two elementary beams 30 and 31 diametrally opposed and turning at an equal distance from the second optical axis 2. This arrangement is generally preferable to the arrangement which employs only a single elementary beam in view of the greater precision which is obtainable.

As a variant of the embodiment shown on FIG. 3, one might have in place of the channels 25, 26 and 36 as provided in the glass plate 35, optical fibers having the same arrangement as such channels and arranged in the drum in a manner similar to that which has been shown on FIG. 2. Such optical fibers are known under the name of couplers in the telecommunications art.

The first embodiment of the invention described in respect of FIGS. 2 and 3 permits the generation of only one luminous tubular beam. Such arrangement is thus applicable only in the case where there is envisaged only a single power beam, the cross-section of which is fixed and well determined. In numerous cases, however, the surgeon must be able to choose between power beams exhibiting at least two different cross-sections, the dimension of the beam defining a cone having a predetermined vertex angle after said beam has passed through the converging lens 41 (FIG. 1). A cone having a relatively large vertex angle, for instance 16°, is preferred for the reduced depth of field exhibited by its focal distance and thus the precision of location of the point where the surgical treatment must be applied. Such an angle is likewise preferred in the case of the employment of a pulsed laser developing high power. On occasion, however, such an opening angle prevents attaining certain places within the eye as for instance that shown on FIG. 1 which is close to the angle between the iris and cornea. In this case, it is necessary to reduce the opening angle of the treatment cone by half, i.e. 8° for instance.

The modification of the opening angle of the treatment cone is brought about as has been mentioned in respect of FIG. 1, by a diaphragm 131 or an optical arrangement 24 which modifies the cross-section of the power beam 34 which here is shown in the form of a cylinder of diameter $D_1$ prior to its passage through the converging lens 41. In correspondence to this, it is thus necessary to modify the diameter $D_2$ of the tubular luminous beam which must continue to envelop the power beam. One thus arrives at the second embodiment of the invention which enables such modification, while maintaining use of the homogeneous light guides, the object of the first embodiment of the invention. Two cases may be presented according to whether this modification of diameter $D_2$ is brought about in a continuous manner or by steps.

Figure 4:
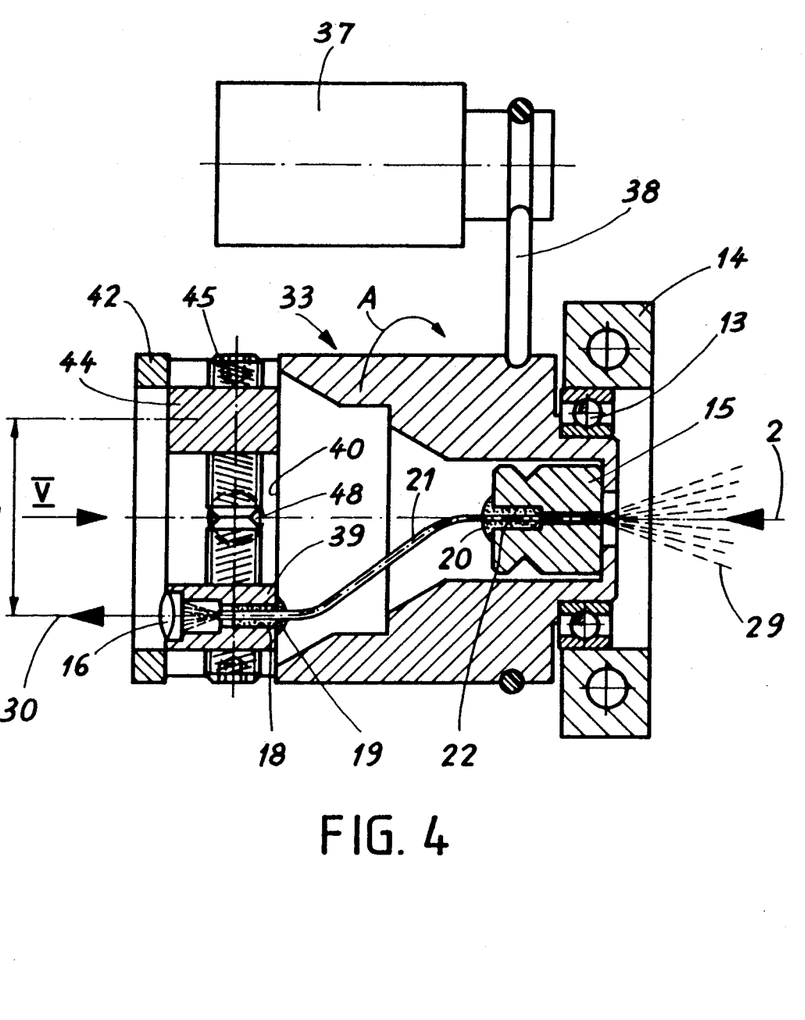
FIG. 4 is a cross-section through the rotating element referenced 33 on FIG. 1 and obtained in accordance with a second embodiment of the invention.
Figure 5:
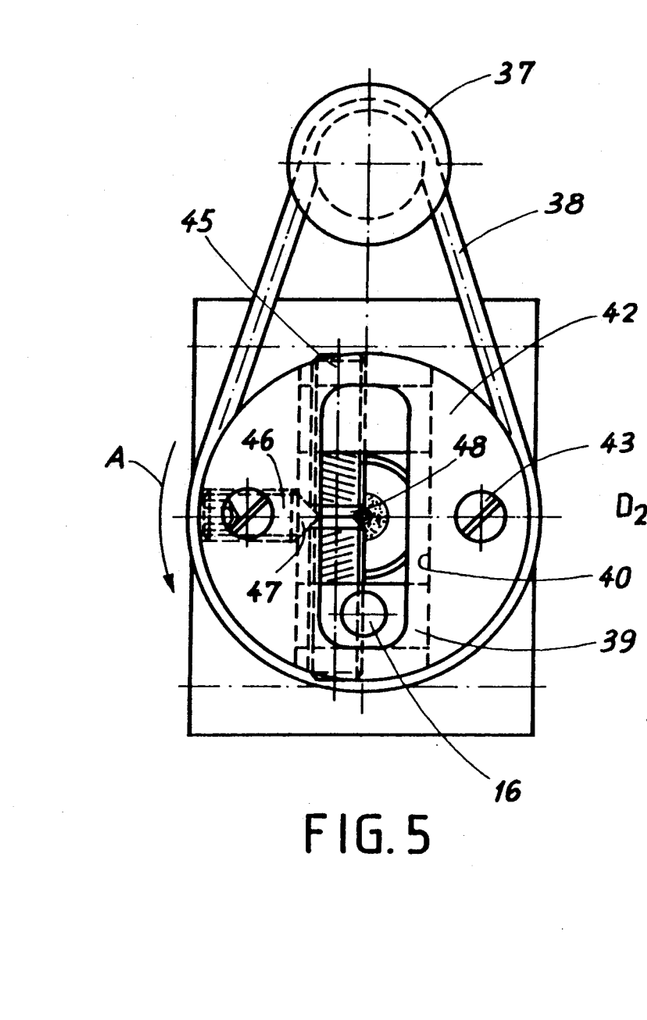
FIG. 5 is a view along arrow V of FIG. 4.

FIGS. 4 and 5 show a rotating element 33 arranged to bring about variation in a continuous manner of the diameter $D_2$ of the luminous tubular beam corresponding with the diameter $D_1$ chosen for the cylinder of the power beam. This second embodiment of the invention includes again a drum turning in the sense of the arrow A and being inserted into the schematic of FIG. 1 in place of the block bearing reference 33. Rotation of the drum is assured by a motor 37 coupled to the drum by means of a belt 38. The drum turns in a fixed frame 14 to which it is attached by means of a ball bearing 13. The light beam 29 emitted by the second light source 28 (FIG. 1) penetrates into a homogeneous light guide 21. In this manner the beam 29 is transformed into an elementary beam 30 offset relative to the rotation axis 2 of the drum. When the drum turns, the elementary beam 30 generates a luminous tubular beam 32 (FIG. 1).

One end of guide 21 penetrates into an orifice 22 pierced into a cylindrical element 15 fixed to the drum. The other end of the guide 21 penetrates into another orifice 18 pierced into a transporter 39 capable of sliding in a slot 40. The slot 40 is formed on one hand by a groove provided in the drum and on the other hand by a cover 42 which covers the drum and which is fixed thereto by means of screw 43. The slot 40 accommodates a further transporter 44 which is the duplicate of the first transporter but which is not provided with an orifice. The two transporters are made to slide in the groove by operating an endless screw 45 fitted into corresponding threadings provided in the transporters. As is shown on FIGS. 4 and 5, the endless screw includes a screw thread which is reversed at the center of said screw. In this manner it is understood that when one turns the screw 45 in one sense the transporters are separated and when one turns said screw in the other sense the transporters are brought closer to one another. A blocking screw 46 enables fixing the position of the transporters when the working diameter of the luminous tubular beam has been chosen. To this end screw 46 is terminated by a point 47 adapted to penetrate into a groove 48 provided in the endless screw.

As was already the case for the transporter of FIG. 2, guide 21 is here an optical fiber fixed to element 15 and to transporter 39 by means of glue points referenced respectively as 20 and 19. In the same manner, transporter 39 includes a lens 16 intended to render parallel the light beams emitted by guide 21 and forming the elementary beam 30.

Figures 6, 7:
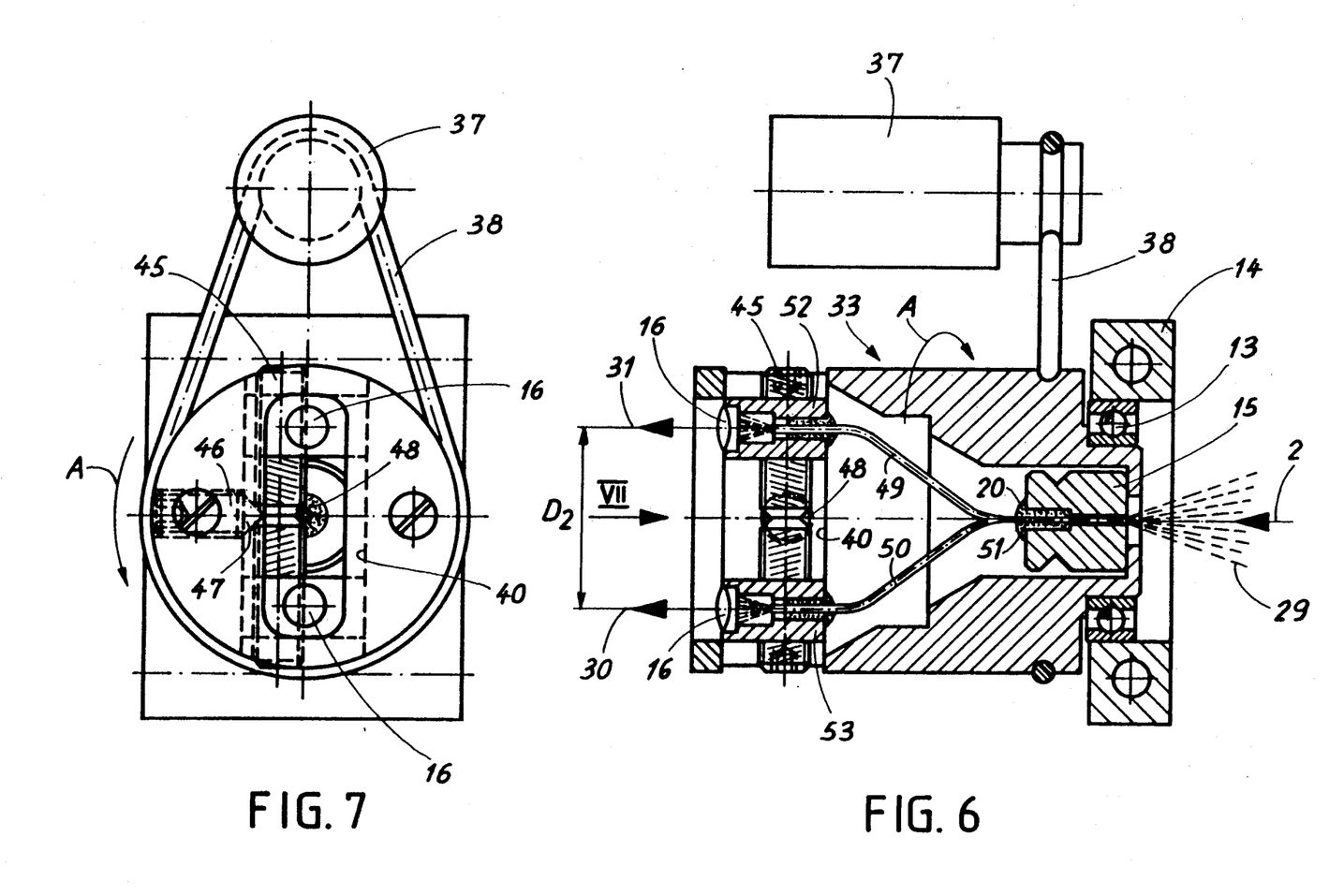
FIG. 6 is a cross-section through the rotating element referenced 33 on FIG. 1 and obtained according to a first variant of the second embodiment of the invention.
FIG. 7 is a view along arrow VII of FIG. 6.

FIGS. 6 and 7 show a first variant of the second embodiment of the invention. Here the rotating element 33 includes two coupled optical fibers exhibiting the form of a Y. The lower branch 51 of the Y attached to element 15 by the glue point 20 receives the light beam 29 while each of the upper branches 49 and 50 of the Y is received in a transporter 52, 53 mounted in the rotating element 33 in the same manner as has been described with reference to FIGS. 4 and 5. There are thus produced two elementary beams 30 and 31 which generate when the drum rotates, a luminous tubular beam 32 (FIG. 1), the diameter $D_2$ of this beam being susceptible to be varied through operating on the endless screw 45.

Figure 8:
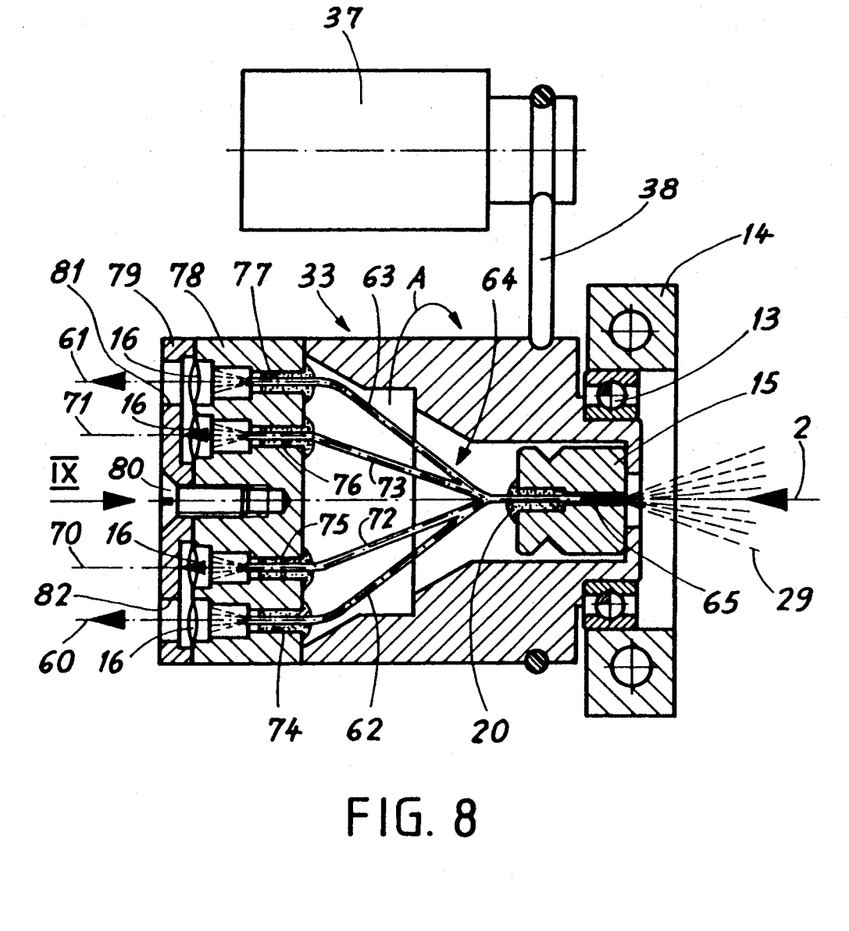
FIG. 8 is a cross-section through the rotating element referenced 33 on FIG. 1 and obtained according to a second variant of the second embodiment of the invention.
Figure 9:
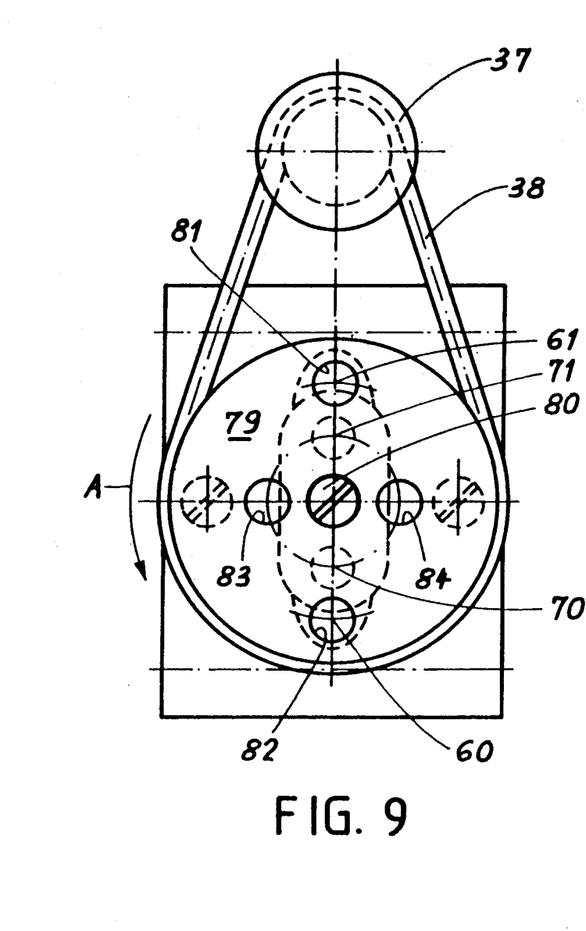
FIG. 9 is a view along arrow IX of FIG. 8.

FIGS. 8 and 9 show a second variant of the second embodiment of the invention. This variant enables choosing two different diameters $D_2$ for the luminous tubular beam for instance a small diameter in order to produce a cone having a vertex angle of 8° and a large diameter to produce a cone having a vertex angle of 16° (values mentioned hereinabove). To this end the rotating element 33 includes first means in order to transform beam 29 issuing from the second light source into first 60, 61, and second 70, 71 pairs of elementary beams. These means include a homogeneous light guide 64 developing in a tree-like manner as may be seen on FIG. 8. The elementary beams 60, 61 generating a luminous tubular beam of large diameter are produced by homogeneous guides 62, 63 and the elementary beams 70, 71 generating a luminous tubular beam of small diameter are produced by the homogeneous guides 72, 73. Guide 64 is an optical fiber of the type used for instance in telecommunications and known under the name of a coupler. The end 65 of guide 64 is fastened in the manner already described to a cylindrical element 15 fixed to the rotating element 33. This end 65 receives the beam 29. The other ends of guides 62, 63, 72 and 73 are placed into orifices referenced 74 to 77 pierced into a closing plate 78. Aligned in these orifices are found lenses 16 having a function as has been explained hereinabove.

The selection means as between the tubular beam generated by the elementary beams 60 and 61 and the tubular beam generated by the elementary beams 70 and 71 is obtained by placing in front of plate 78 a disc 79 pierced with four holes, the disc being maintained on the plate by means of a screw 80. If one chooses beams 60 and 61, disc 79 will be oriented in a manner such that holes 81 and 82 allow passage of these beams as has been shown on FIGS. 8 and 9. Should one choose beams 70 and 71, the disc 78 will be rotated through 90° in which case the beams 70 and 71 will be able to pass through holes 83 and 84, the beams 60 and 61 in this case being blocked.

Figure 10:
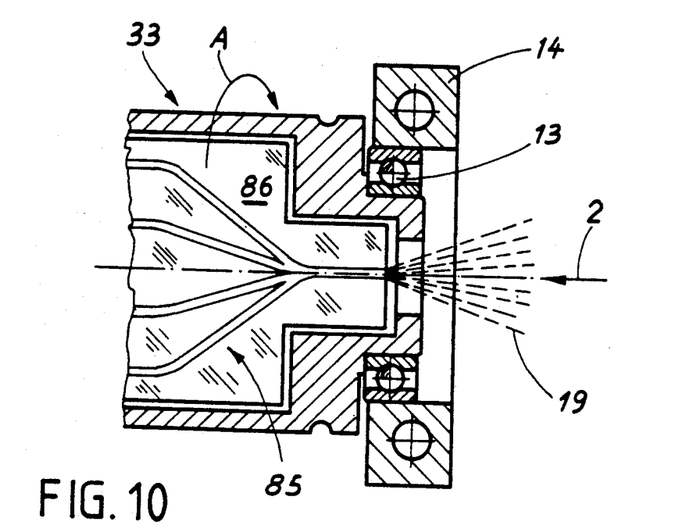
FIG. 10 is a partial cross-section through the rotating element referenced 33 on FIG. 1 and obtained in accordance with a third variant of the second embodiment of the invention.

A third variant of the second embodiment of the invention is shown in the partial cross-section of FIG. 10. Here the optical fiber 64 of FIG. 8 is replaced by channels 85 obtained by doping a glass plate 86. This construction is closely related to that discussed with reference to FIG. 3. The result obtained is however the same as that set out with reference to FIGS. 8 and 9. Here there will be found the same selection means, i.e. the rotation of a plate pierced with four holes.

In certain cases of employment of the apparatus herein described, one would wish to vary the luminous intensity of the elementary beams emitted by the rotating element. This may be effected by means of an attenuator situated between the second light source 28 and the rotating element 33 (FIG. 1).

Figure 11:
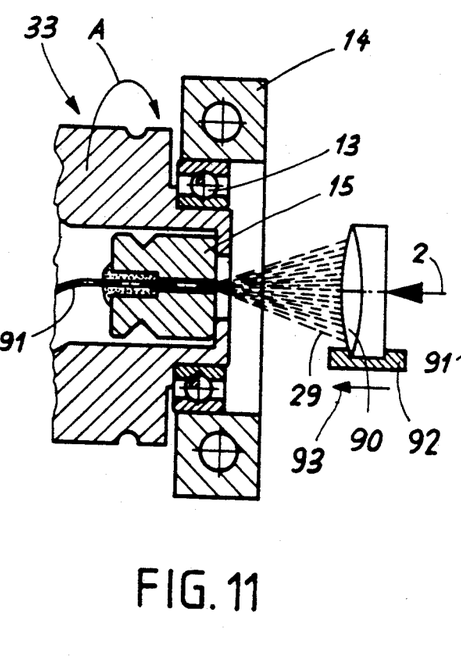
FIG. 11 is a partial cross-sectional view illustrating a lens attenuator in a position to focus a light beam on the end of an optical fiber.
Figure 12:
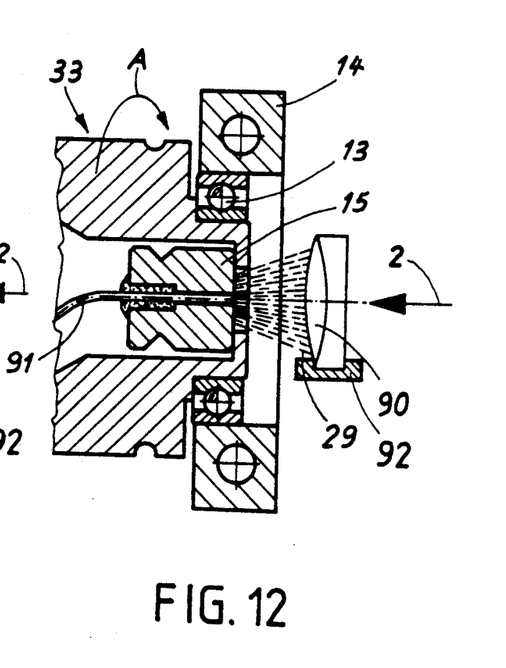
FIG. 12 is a partial cross-sectional view illustrating a lens attenuator in a defocused position relative to the end of an optical fiber.

Advantageously, such attenuator is a transporter 92 bearing a lens 90 the output rays of which converge towards the rotating element as is shown on FIGS. 11 and 12. The beam 29 issuing from source 28 (FIG. 1) is rendered convergent by lens 90. This beam penetrates the end of the light guide 91 as realized by any of the means described hereinbefore. FIG. 11 shows that all of beam 29 may penetrate into guide 91. In this case there is obtained a maximum intensity of the light. Should one defocus lens 90 by driving the transporter in the sense of arrow 93, only a portion of the light will attain guide 91 as may be seen on FIG. 12. One has thus by this means obtained a light attenuator of great simplicity and efficiency.

What I claim is:

1. A surgical treatment device, in particular for ophthalmological purposes comprising:
   at least one first light source emitting a power beam along a first optical axis and having a predetermined cross-section,
   a second light source emitting a visible light beam along a second optical axis,
   a rotating element rotating around said second optical axis, said element including means for transforming the beam issuing from said second source into at least one elementary beam turning around said second optical axis and arranged to form a luminous tubular beam intended to surround said power beam,
   means for combining said power beam and said luminous tubular beam along a third common optical axis, and
   a lens arranged in the path of the third optical axis so as to concentrate said power beam and said luminous tubular beam which surrounds it onto the focal point of the lens in accordance with a core having a predetermined vertex angle,
   wherein the transforming means forming part of said rotating element include at least one homogeneous light guide.

2. A surgical treatment device as set forth in claim 1 wherein the homogeneous light guide comprises an optical fiber.

3. A surgical treatment device as set forth in claim 1 wherein said rotating element includes means for transforming the beam issuing from said second source into two elementary beams and said transforming means include two homogeneous light guides.

4. A surgical treatment device as set forth in claim 3 wherein the homogeneous light guides comprise coupled optical fibers.

5. A surgical treatment device as set forth in claim 3 wherein the homogeneous light guides comprise channels obtained by doping a glass plate.

6. A surgical treatment device as set forth in claim 1 wherein between the second light source and the rotating element there is placed an attenuator enabling varying of the light intensity of the elementary beam or beams.

7. A surgical treatment device as set forth in claim 6 wherein the attenuator is a transporter bearing a lens the output rays of which converge toward the rotating element, said transporter being adapted to approach the rotating element in order to diminish the quantity of light entering said element by defocussing said lens.

8. A surgical treatment device, in particular for ophthalmological purposes, comprising:
   at least one first light source emitting a power beam along a first optical axis and which has a cross section which may be varied,
   a second light source emitting a visible light beam along a second optical axis,
   a rotating element rotating around said second optical axis, said element including first means for transforming the beam issuing from said second source into at least one elementary beam turning around said second optical axis and arranged to form a luminous tubular beam intended to surround said power beam,
   means for combining said power beam and said luminous tubular beam along a third common optical axis, and
   a lens arranged in the path of said third optical axis for concentrating said power beam and said luminous tubular beam which surrounds it onto the focal point of the lens in accordance with a cone having a predetermined vertex angle,
   wherein the first means forming part of the rotating element include at least one homogeneous light guide, said rotating element further comprising second means for varying the diameter ($D_2$) exhibited by the luminous tubular beam in a manner such that it surrounds the power beam in correspondence with the cross section ($D_1$) chosen for said power beam.

9. A surgical treatment device as set forth in claim 8 wherein the rotating element includes first means for transforming the beam issuing from said second source into two elementary beams, said first means comprising two coupled optical fibers exhibiting the form of a Y and that the second means includes an arrangement enabling the bringing together or the spreading apart of the two upper branches of the Y from one another about said second optical axis.

10. A surgical treatment device as set forth in claim 9 wherein said arrangement includes two transporters each bearing the end of an optical fiber forming an upper branch of the Y, the transporters being adapted to slide in a guideway under the urging of an endless screw having its threading reversed midway along the length thereof in order to spread apart or bring together said transporters relative to one another according to whether the endless screw is rotated respectively in a first or in a second sense.

11. A surgical treatment device as set forth in claim 8 wherein the rotating element includes first means for transforming the beam issuing from the second source into first and second pairs of elementary beams, said first means comprising a homogeneous light guide developing in a treelike manner so as to form when driven in rotation by the rotating element, first and second coaxial luminous tubular beams of different diameters and said second means include an element enabling the selection of one or the other of said pairs of elementary beams 12. A surgical treatment device as set forth in claim 11 wherein the homogeneous light guide developing in a treelike manner is formed by optical fibers.

13. A surgical treatment device as set forth in claim 11 wherein the homogeneous light guide developing in a tree-like manner is formed by channels obtained by doping a glass plate.

14. A surgical treatment device as set forth in claim 11 wherein said selection element includes a plate having holes therein adapted to be arranged in a first position in which it allows passage of the first pair of elementary beams or in a second position in which it allows passage of the second pair of elementary beams.

15. A surgical treatment device as set forth in claim 8 wherein between the second light source and the rotating element there is placed an attenuator enabling varying of the light intensity of the elementary beam or beams.

16. A surgical treatment device as set forth in claim 15 wherein the attenuator is a transporter bearing a lens the output rays of which converge toward the rotating element, said transporter being adapted to approach the rotating element in order to diminish the quantity of light entering said element by defocussing said lens.

* * * * *